United States Patent [19]

Beaton et al.

[11] Patent Number: 5,278,495
[45] Date of Patent: Jan. 11, 1994

[54] MEMORY AND APPARATUS FOR A THERMALLY ACCELERATED RELIABILITY TESTING

[75] Inventors: Bradford P. Beaton; Michael C. Rankin, both of West Columbia; Frederick D. Brumble, Columbia, all of S.C.

[73] Assignee: NCR Corporation, Dayton, Ohio

[21] Appl. No.: 84,789

[22] Filed: Jun. 29, 1993

Related U.S. Application Data

[63] Continuation of Ser. No. 790,608, Nov. 8, 1991, abandoned.

[51] Int. Cl.⁵ .................... G01R 31/02; H01L 23/44
[52] U.S. Cl. ............................ 324/158 F; 165/80.4
[58] Field of Search ............... 324/158 R, 158 F, 731; 374/45, 57; 361/385, 384, 383; 165/80.4; 73/865.6

[56] References Cited

U.S. PATENT DOCUMENTS

| | | | |
|---|---|---|---|
| 3,710,251 | 1/1973 | Hagge et al. | 324/158 F |
| 3,761,808 | 9/1973 | Ryan | 324/73 R |
| 3,807,216 | 4/1974 | Lindwedel | 73/865.6 |
| 4,026,412 | 5/1987 | Henson | 324/158 F |
| 4,115,736 | 9/1978 | Tracy | 324/158 F |
| 4,172,993 | 10/1979 | Leach | 324/158 F |
| 4,483,629 | 11/1984 | Schwarz | 374/57 |
| 4,607,220 | 8/1986 | Hollman | 324/158 F |
| 4,745,354 | 5/1988 | Fraser | 324/73 R |
| 4,787,752 | 11/1988 | Fraser et al. | 374/45 |
| 4,791,364 | 12/1988 | Kufis et al. | 324/158 F |
| 4,838,041 | 6/1989 | Bellows et al. | 361/383 |
| 4,870,355 | 9/1989 | Kufis et al. | 324/158 F |
| 4,945,302 | 7/1990 | Janum | 324/73.1 |
| 4,954,774 | 9/1990 | Binet | 324/158 F |
| 4,962,355 | 10/1990 | Holderfield et al. | 324/158 F |
| 4,982,153 | 1/1991 | Collins et al. | 324/158 R |
| 5,004,973 | 4/1991 | Taraci et al. | 324/158 F |
| 5,015,337 | 5/1991 | Fraser | 202/169 |
| 5,039,228 | 8/1991 | Chalmers | 374/57 |
| 5,063,475 | 11/1991 | Balan | 361/384 |
| 5,084,671 | 1/1992 | Miyata et al. | 324/158 F |
| 5,086,269 | 2/1992 | Nobi | 324/158 F |
| 5,097,207 | 3/1992 | Blanz | 324/158 F |
| 5,187,432 | 2/1993 | Bauernfeind et al. | 324/158 R |

*Primary Examiner*—Vinh Nguyen
*Attorney, Agent, or Firm*—Paul W. Martin; Jack R. Penrod

[57] ABSTRACT

A method for rapidly changing temperatures of either an unpopulated printed circuit board or a completed printed circuit board assembly and testing operation thereof. The rapid temperature change nondestructively stresses the printed circuit board or assembly and uncovers many defects that are hard to discover by constant temperature test methods. Each unit under test is alternately bathed with cold perfluorinated liquid and hot perflourinated liquid to rapidly change it temperature from cold (273 degrees kelvin) to hot (333 degrees kelvin).

16 Claims, 2 Drawing Sheets

MEMORY AND APPARATUS FOR A THERMALLY ACCELERATED RELIABILITY TESTING

This is a continuation of co-pending application Ser. No. 07/790,608 filed on Nov. 8, 1991, now abandoned.

BACKGROUND OF THE INVENTION

The present invention relates to a test method and apparatus and more particularly to a test method and apparatus for accelerated reliability testing.

The use of high temperatures and low temperatures as a means to stress electrical and electronic components in order to uncover weaknesses and faults without damaging healthy components is well known. Military standard Mil-Std-785B, Task 301 addresses the use of environmental stress as a method of inducing early failures due to part weaknesses and workmanship defects.

U.S. Pat. No. 3,710,251 issued to Holderfield et al. discloses a fixture for holding an unmounted microelectronic die or wafer and subjecting the microelectronic die or wafer to hot and cold temperatures while performing circuit tests. The hot and cold temperatures are derived from hot and cold liquids respectively and transferred through the holding fixture to the die or wafer. At column 2, lines 29-33 mention that rapid cycling between high and low temperatures is possible if such is required for circuit testing.

U.S. Pat. No. 4,870,355 issued to Kufis et al. discloses a fixture for holding a die or wafer and directly heating or cooling the die or wafer with hot or cold nitrogen gas.

U.S. Pat. No. 4,962,355 issued to Holderfield et al. discloses a fixture for heating or cooling a single electronic device, such as a hybrid semiconductor chip, with an unspecified fluid.

U.S. Pat. No. 4,945,302 issued to Janum discloses a test circuit board for mounting a plurality of microelectronic circuit and then subjecting part of the test circuit board and the microelectronic circuits thereon to elevated temperatures as a burn in procedure. The other part of the circuit board has test support circuits thereon and is not subjected to the elevated temperatures.

These patents all have the short coming that they do not disclose a method or an apparatus for testing a production printed circuit board (PCB), or a PCB assembly that has many electrical and electronic components attached thereto and inter-connected thereby. Yet each PCB assembly represents a considerable investment by the manufacturer, so it is desirable to uncover and repair any fault or weakness on each PCB and on each PCB assembly.

Thus, it is an object of the present invention to provide a test apparatus for mounting a PCB or PCB assembly, testing the operation of the PCB assembly during rapid temperature cycling of the entire circuit board and all the electrical and electronic components thereon.

It is another object of the present invention to provide a test method for testing a PCB or a PCB assembly during rapid temperature cycling in order to uncover weaknesses and faults thereof.

SUMMARY OF THE INVENTION

Briefly stated, in accordance with one aspect of the invention the foregoing objects are achieved by providing a method for testing a PCB or PCB assembly, including a PCB and electrical and electronic components that are connected thereto. The method includes the steps of inserting the PCB assembly in a circuit board connector that is part of a test apparatus; enclosing the PCB assembly and the circuit board connector within a liquid-tight enclosure; filling the enclosure with a first liquid having a first temperature to affect the temperature of the PCB assembly to rapidly move to the first temperature; draining the first liquid from the enclosure such that the PCB assembly is no longer covered; and subsequently filling the enclosure with a second liquid having a second temperature to affect the temperature of the PCB assembly to rapidly move to the second temperature. Operation of the PCB assembly is tested at the first temperature, during the change from the first temperature to the second temperature, and at the second temperature.

In another aspect of the invention, the aforementioned objects may be achieved by providing an apparatus for testing a printed circuit board assembly, including a PCB and at least one electronic component that is connection thereto as a PCB assembly. The apparatus includes a connector for inserting the PCB assembly; a device for enclosing the PCB assembly and the connector, the enclosing device being liquid-tight; a device for filling the enclosing device with a first liquid having a first temperature to affect the temperature of the PCB assembly to rapidly move to the first temperature; a device for draining the first liquid from the enclosing device and subsequently filling the enclosing device with a second liquid having a second temperature to affect the temperature of the PCB assembly to rapidly move to the second temperature. The apparatus also includes a device for testing the operation of the PCB assembly at the first temperature, during the change from the first temperature to the second temperature, and at the second temperature.

BRIEF DESCRIPTION OF THE DRAWINGS

While the specification concludes with the appended claims particularly pointing out and distinctly claiming the subject matter which is regarded as the invention, it is believed that the invention will be better understood from the following description taken in conjunction with the accompanying drawings in which:

DETAILED DESCRIPTION

Figure 1:
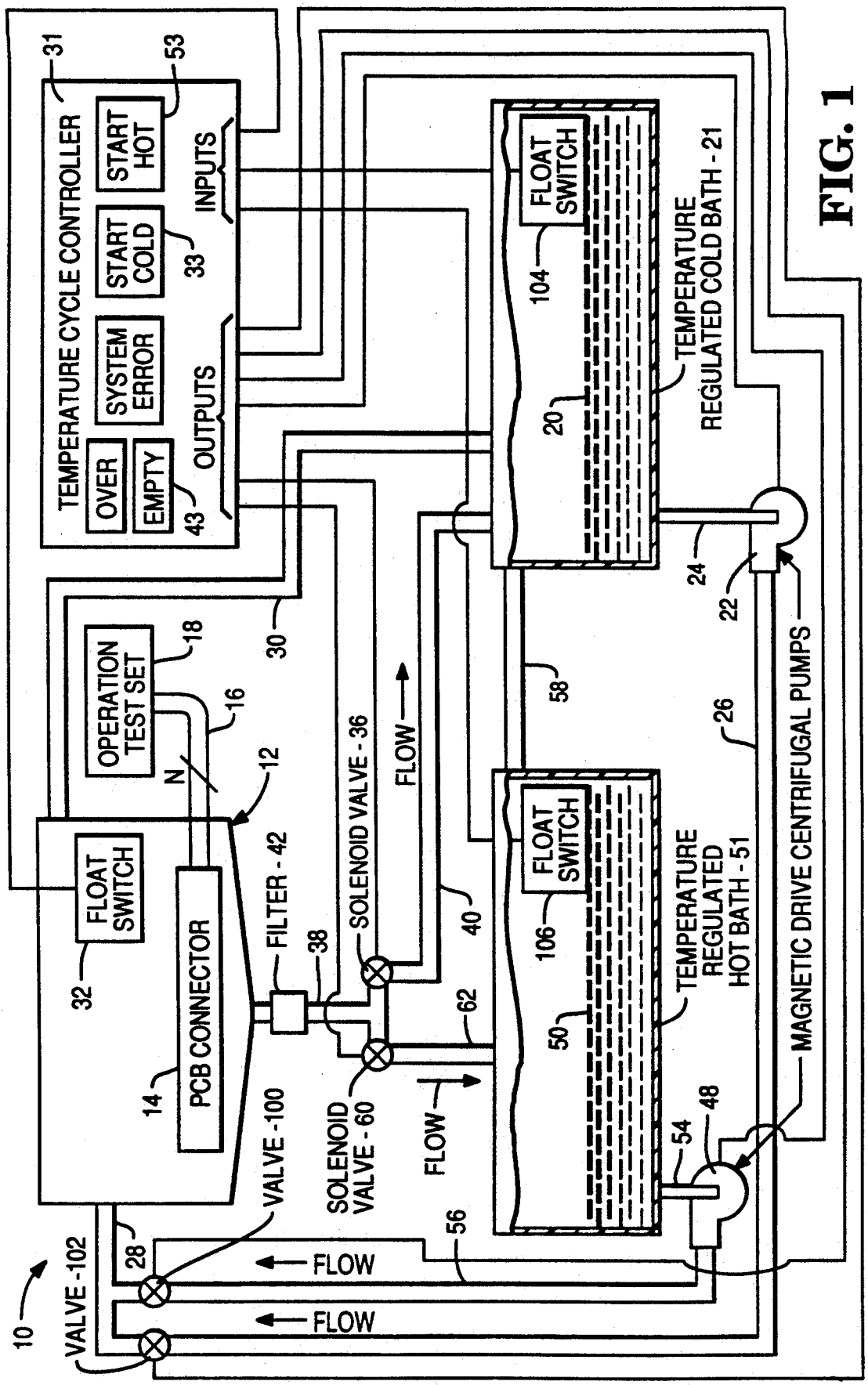
FIG. 1 is a block diagram of a test apparatus according to the invention.

Referring now to FIG. 1, an apparatus 10 for testing electrical or electronic assemblies is shown in block diagram form. The test apparatus 10 has a test enclosure 12. For reasons that will be explained below, the enclosure 12 is liquid-tight. Inside the enclosure 12 is a connector 14 for receiving and connecting to a PCB or PCB assembly to be tested (not shown in FIG. 1). The connector 14 is connected by cable 16 that is made up of N conductors to an operation test set 18. The operation test set controls the supply of power to the PCB or PCB assembly under test, and also samples responses of the PCB or PCB assembly to test stimuli in order to determine proper or improper performance of the PCB or PCB assembly.

The test apparatus 10 is preferably used to locate faults on PCB assemblies, however it also has been used to screen test bare PCBs before assembly to check for printed conductor and via/through-hole faults before the electrical and electronic components are added to make up a PCB assembly. The make up of the operation test set 18 is sufficient to test either bare PCBs or PCB assemblies.

The connector 14 can be a separate connector if the PCB or PCB assembly under test is self sufficient, or it can be a connector of a larger system. If the connector 14 is part of a larger system, then the enclosure 12 may enclose only enough of the larger system to perform the operational test. For reasons that will be explained below, the enclosure 12 is preferably vapor-tight during the performance of the operational tests.

Once the PCB or PCB assembly under test is in the connector 14 and the operation test is started, a liquid 20 is pumped by pump 22 from cold bath 21 through pipes 24, 26 and 28 into the enclosure 12. The liquid 20 is a perfluorinated liquid, such as Fluorinert, which is a registered trademark of 3M Corporation, Minneapolis, Minn. The liquid 20 is approximately twice as dense as water, so it is capable of absorbing large quantities of heat from the PCB or PCB assembly to the colder fluid 20. Since the fluid 20 may cost as much as $400 a gallon, leakage of the fluid 20 or vapors thereof are prevented wherever possible. To this end, a pipe 30 vents the vapor that is displaced from the enclosure 12 as the enclosure 12 is filled by the liquid 20 back into the cold bath 21. At the cold bath 21, any vapor therein is cooled. This cooling causes most of the liquid 20 that is evaporated and contained therein is condensed back into liquid form and becomes part of the liquid 20 again.

A controller 31 starts the filling of the enclosure 12 with the liquid 20 when the operator activates the start cold switch 33. The liquid 20 is subsequently pumped into the enclosure 12 until a float switch 32 by its position afloat in the liquid 20 is activated and indicates that the enclosure 12 is sufficiently full. The float switch 32 by operator action or by action of a simple switching circuit stops further filling.

The liquid 20 is cooled to a low temperature, such as 273 degrees kelvin or lower, and since the liquid 20 has a high density and a high heat capacity it can absorb heat from the PCB or PCB assembly under test very rapidly. Thus, in a short time the PCB or PCB assembly will be cooled down to essentially 273 degrees kelvin. After substantially reaching the first temperature and a short delay, which may be as long as the controller 31 takes to stop the pump 22 and open the valve 36, the liquid 20 is drained through pipes 38, 40 into the cold bath 21. A filter 42 is preferably included between the enclosure 12 and the pipe 38 to filter out water, hydrofloric acid formed by the action of water on perfluorinated liquids, any other liquid contaminates, and particulate matter from the PCB or PCB assembly under test and the apparatus 10.

As the liquid 20 drains into the cold bath 21, vapor from which most of the evaporated perfluorinated liquid has been condensed is both driven and drawn from the cold bath 21 into the enclosure 12.

Once the liquid 20 has been drained, the float switch 32 assumes the full down position, which corresponds substantially to the empty condition of the enclosure 12.

At this point, a sensor, such as the float switch 32, turns the empty indicator 43 ON, indicating that the apparatus is prepared to start the cold-to-hot transition portion of the operation test cycle.

To start the cold-to-hot transition, the controller 31 under operator control by actuation of switch 53, or under automatic control if the controller 31 is so designed, energizes pump 48 and pumps liquid 50 out of the hot bath 51. The pump 48 pumps the liquid 50 from the hot bath 51 through pipes 54, 56, 28 to the enclosure 12. The liquid 50 is pumped into the enclosure 12 until the float switch 32 is again actuated, at which time the pumping ceases. As before, the location of the float switch 32 is selected such that the PCB or PCB assembly is completely immersed in the liquid 50.

Preferably, the liquid 50 is chemically the same as the liquid 20, in order to lessen problems of the two liquids mixing. The liquid 50 is heated within the hot bath 51 to a temperature of at least 333 degrees kelvin, and preferably to a temperature of 343 degrees kelvin. The temperature of 343 degrees kelvin, i.e. 70 degree Celsius, is close to the operating maximum of some electronic components. If such components are used, then the temperature of 333 degrees kelvin should be used, otherwise the higher temperature gives the greater temperature transition and hence the greater fault detecting stress on the PCB or PCB assembly under test.

At temperatures of 333 degrees kelvin or more, the liquid 50 will evaporate more readily than at room temperature. This being the case, it is even more important to have the enclosure 12 vapor tight for this portion of the test than during the cold portion of the test. The hot liquid 50 as it is pumped into the enclosure 12 will give off vapors which will be displaced as the enclosure is filled with liquid. To provide another closed venting action, the hot bath 51 is connected to the cold bath 21 by pipe 58. Thus, as vapor is displaced from the enclosure 12, the vapor is routed through the cold bath 21. In the cold bath 21, the vapor has a chance to cool and condense a part of its evaporated Fluorinert before some of it is drawn into the hot bath 51 in order to take the place of the liquid 50 that was pumped into the enclosure 12.

The high density and high heat capacity of the liquid 50 provides the means for transferring heat to the PCB or PCB assembly under test in order to rapidly increase its temperature to at least 333 degree kelvin. The placement of the float switch 32 or a deliberated delay may be inserted in the test if necessary to permit the PCB or PCB assembly under test to warm up to the temperature of the liquid 50. After the PCB or PCB assembly has been tested at the temperature of the liquid 50, the enclosure 12 is drained by opening a valve 60 and allowing the liquid 50 to drain through the filter 42, the pipe 38, the valve 60 and the pipe 62 into the hot bath 51.

As the hot bath 51 is filled by the liquid 50 returning from the enclosure 12, the hot vapor displaced thereby is driven and drawn through the pipe 58 into the cold bath 21 where it is cooled and most of the evaporated liquid therein is condensed therefrom. The enclosure 12 as it drains draws a cooled vapor through the pipe 30 from the cold bath 21 as the liquid 50 drains back to the hot bath 51. In this manner, the cold bath 21 is used also as a condensing means to recover some of the vapor borne Fluorinert that would otherwise escape and be lost to the atmosphere.

When the liquid 50 is substantially drained from the enclosure, the float switch 32 again is activated to indicate that the enclosure 12 is again empty and prepared to be filled. This completes one full temperature cycle.

Figure 2:
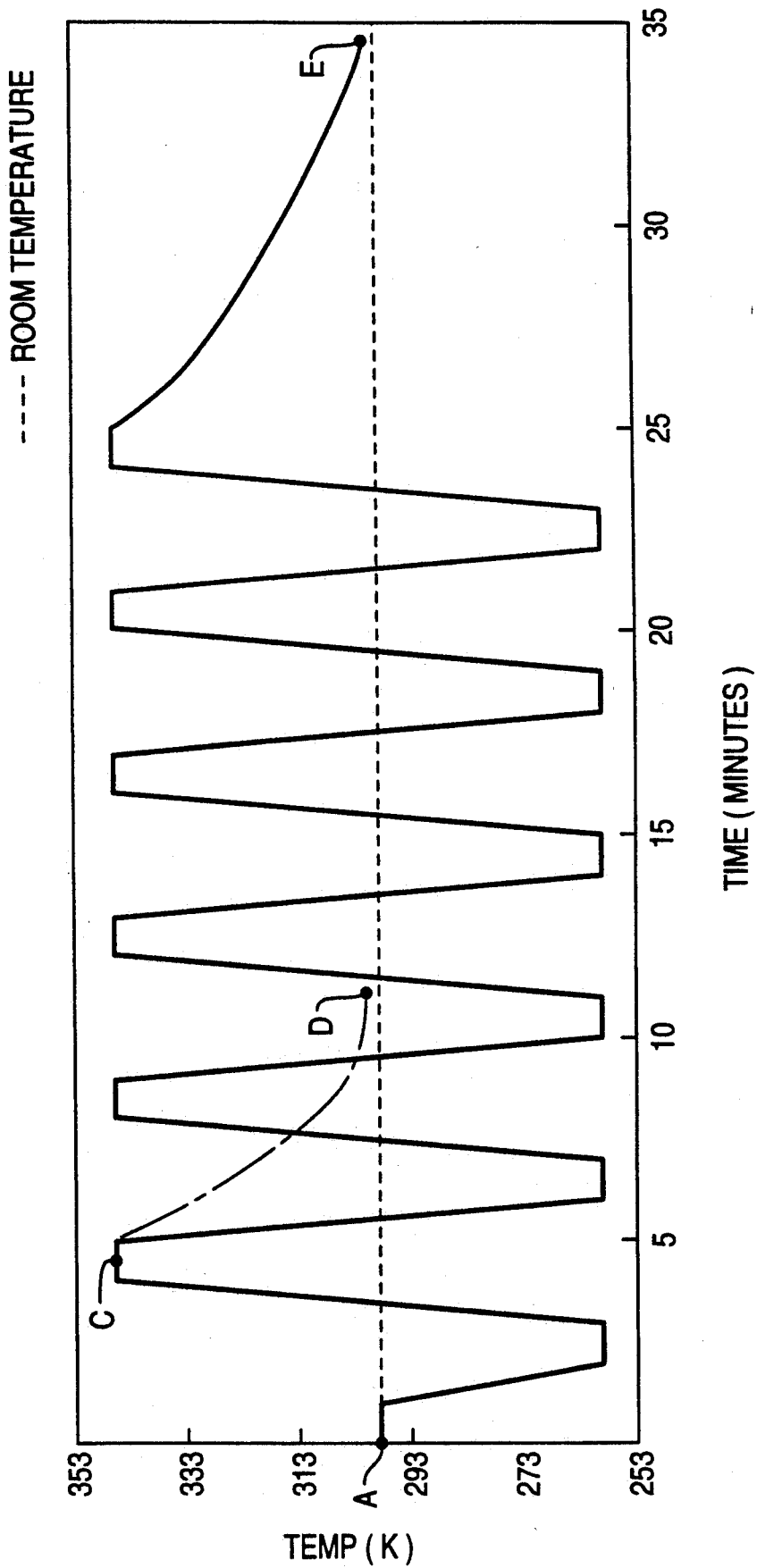
FIG. 2 is a graphic representation of a set of temperature cycles that could be performed by the apparatus shown in FIG. 1.

Referring to FIG. 2, the description above describes a method of testing a PCB or PCB assembly as it is temperature cycled from point A, to point B, to point C, and is cooling down to point D (if the enclosure 12 is not filled again with either the liquid 20 or the liquid 50). As FIG. 2 indicates, a PCB or PCB assembly under test can be subjected to multiple dynamic temperature stresses as a way to uncover faults and defects. Since the test apparatus 10 takes energy to heat the hot bath 51 and to cool the cold bath 21, and since it takes a technician's time to perform the testing, a trade off must be made between the cost of running a longer test versus the savings of uncovering additional faults. As shown in FIG. 2, a test period of approximately 30 minutes has been found previously to be reasonable.

Referring again to FIG. 1, at the conclusion of each test of a PCB or PCB assembly, the enclosure 12 is opened up and the PCB or PCB assembly is removed from the connector 14. There will always be a small quantity of Fluorinert 'dragged out' of the enclosure 12 by clinging to various surfaces and collecting in small aperatures of the PCB or PCB assembly, so some Fluorinert is lost with this test method.

To prevent mixing of the hot and cold liquids 50, 20, it may be desirable to have valves 100 and 102 as part of the apparatus 10 to separate and limit such mixing. The valves may be controlled by the controller 31 as shown, or for example, could also be one way check valves. Controlled valves 100, and 102 can be closed for emergency situations to halt flows of liquids 20 and 50 into the enclosure 12. The valves 100, 102 along with valves 36 and 60 could be used to substantially stop all flow of fluid within the apparatus 10. Such a stop could be initiated by the action of either over flow float switch 104 or 106. The expense and trouble of an overflow of Fluorinert at the cold bath 21 or the hot bath 51 warrants the precaution of an emergency stop capability if the flow in the apparatus 10 becomes imbalanced or clogged. Those skilled in the art will recognize that if the valves 100, 102, 60, and 36 are closed for an emergency, the pumps 48 and 22 should stop when the valves 100, 102, 60, and 36 are all closed until the operator can make repairs and safe operation testing can resume.

Thus, it will now be understood that there has been disclosed a method and apparatus for thermally accelerated reliability testing for a PCB or a PCB assembly. While the invention has been particularly illustrated and described with reference to preferred embodiments thereof, it will be understood by those skilled in the art that various changes in form, details, and applications may be made therein. For example, some other inert liquid other than Fluorinert may be used. It is accordingly intended that the appended claims shall cover all such changes in form, details and applications which do not depart from the true spirit and scope of the invention.

What is claimed as new and desired to be secured by Letters Patent of the United States is:

1. A method for testing a printed circuit board assembly, including a printed circuit board and electrical and electronic components that are connected thereto, comprising the steps of:

inserting the printed circuit board assembly in a circuit board connector that is part of a test apparatus;

enclosing the printed circuit board assembly and the circuit board connector within a liquid-tight enclosure;

filling the enclosure with a first liquid having a first temperature to affect the temperature of the printed circuit board assembly to rapidly move to the first temperature;

draining the second liquid from the enclosure;

filling the enclosure with a second liquid having a second temperature that is at least sixty Kelvin degrees different from the first temperature to affect the temperature of the printed circuit board assembly to rapidly move to the second temperature; and testing operation of the printed circuit board assembly at the first temperature, during the change from the first temperature to the second temperature, and at the second temperature.

2. A method for testing a printed circuit board assembly as set forth in claim 1, further comprising the steps of:

draining the second liquid from the enclosure;

filling the enclosure with the first liquid having the first temperature to affect the temperature of the printed circuit board assembly to rapidly move to the first temperature; and testing operation of the printed circuit board assembly during the change from the second temperature to the first temperature, and again at the first temperature.

3. A method for testing a printed circuit board assembly as set forth in claim 1, further comprising the steps of:

draining the second liquid from the enclosure;

filling the enclosure with the first liquid having the first temperature to affect the temperature of the printed circuit board assembly to rapidly move to the first temperature;

testing operation of the printed circuit board assembly during the change from the second temperature to the first temperature, and again at the first temperature;

removing all signals from the printed circuit assembly at the completion of testing; and opening the enclosure and removing the printed circuit board assembly from the connector.

4. An apparatus for testing a printed circuit board (PCB) assembly that includes a printed circuit board and at least one electronic component connected thereto, comprising:

a connector for inserting the PCB assembly;

means for enclosing the PCB assembly and the connector, the enclosing means being liquid-tight;

means for filling the enclosing means with a first liquid having a first temperature to affect the temperature of the PCB assembly to rapidly move to the first temperature;

means for draining the first liquid from the enclosing means;

means for filling the enclosing means with a second liquid having a second temperature that is at least sixty Kelvin degrees different from the first temperature to affect the temperature of the PCB assembly to rapidly move to the second temperature; and means for testing operation of the printed circuit board assembly at the first temperature, during the change from the first temperature to the second temperature, and at the second temperature connected to the connector.

5. An apparatus for testing the PCB assembly as set forth in claim 4, further comprising:
a first reservoir for receiving and storing the first liquid as it drains from the enclosing means, the first reservoir having means for maintaining the first liquid at the first temperature.

6. An apparatus for testing the PCB assembly as set forth in claim 5, further comprising:
means for draining the second liquid from the enclosing means; and
means for filling the enclosing means with the first liquid having the first temperature to affect the temperature of the PCB assembly to rapidly move to the first temperature;
whereby, the means for testing operation of the PCB assembly further tests operation of the PCB assembly during the change from the second temperature to the first temperature.

7. An apparatus for testing a printed circuit board assembly as set forth in claim 6, further comprising:
a second reservoir for receiving and storing the second liquid as it drains from the enclosing means, the second reservoir having means for maintaining the second liquid at the second temperature.

8. An apparatus for testing a printed circuit board as set forth in claim 7, further comprising:
means for draining the second liquid from the enclosure into the second reservoir;
means for replacing the second liquid with vapor communicated from the second reservoir through the first reservoir to the enclosing means;
means for filling the enclosing means with the first liquid having the first temperature from the first reservoir to affect the temperature of the PCB assembly to rapidly move to the first temperature; and
means for communicating the vapor displaced from the enclosure into the first reservoir to condense part of the vapor into the first liquid.

9. A method for testing a printed circuit board (PCB) assembly, including a PCB and electrical and electronic components that are connected thereto, comprising the steps of:
inserting the printed circuit board assembly in a circuit board connector that is part of a test apparatus;
enclosing the printed circuit board assembly and the circuit board connector within a liquid-tight enclosure;
filling the enclosure with a first liquid having a first temperature from a first reservoir to affect the temperature of the PCB assembly to rapidly move to the first temperature;
draining the first liquid from the enclosure back into the first reservoir;
filling the enclosure with a second liquid having a second temperature that is at least sixty Kelvin degrees different from the first temperature from a second reservoir to affect the temperature of the PCB assembly to rapidly move to the second temperature; and
testing operation of the PCB assembly at the first temperature, during the change from the first temperature to the second temperature, and at the second temperature.

10. A method for testing the PCB assembly as set forth in claim 9, further comprising the steps of:

draining the second liquid from the enclosure into the second reservoir;
replacing the second liquid with vapor communicated from the second reservoir through the first reservoir to the enclosure;
filling the enclosure with the first liquid having the first temperature from the first reservoir to affect the temperature of the PCB assembly to rapidly move to the first temperature;
communicating the vapor displaced from the enclosure into the first reservoir and condensing part of the vapor into the first liquid; and
testing operation of the PCB assembly during the change from the second temperature to the first temperature, and again at the first temperature.

11. A method for testing the PCB assembly as set forth in claim 9, further comprising the steps of:
draining the second liquid from the enclosure into the second reservoir;
replacing the second liquid with vapor communicated from the second reservoir through the first reservoir to the enclosure;
filling the enclosure with the first liquid having the first temperature from the first reservoir to affect the temperature of the PCB assembly to rapidly move to the first temperature;
communicating the vapor displaced from the enclosure into the first reservoir and condensing part of the vapor into the first liquid; a
testing operation of the PCB assembly during the change from the second temperature to the first temperature, and again at the first temperature;
removing all signals from the PCB assembly at the completion of testing;
draining the first liquid into the first reservoir and at the same time filling the enclosure with vapor communicated from the first reservoir; and
opening the enclosure and removing the PCB assembly from the connector.

12. An apparatus for testing a printed circuit board (PCB) assembly that includes a printed circuit board and at least one electronic component connected thereto, comprising:
a first reservoir;
a second reservoir;
a connector for inserting the PCB assembly;
means for enclosing the PCB assembly and the connector, the enclosing means being liquid-tight;
means for filling the enclosing means with a first liquid from the first reservoir having a first temperature to affect the temperature of the PCB assembly to rapidly move to the first temperature;
means for draining the first liquid from the enclosing means back into the first reservoir;
means for filling the enclosing means with a second liquid from the second reservoir having a second temperature that is at least sixty Kelvin degrees different from the first temperature to affect the temperature of the PCB assembly to rapidly move to the second temperature; and
means for testing operation of the printed circuit board assembly at the first temperature, during the change from the first temperature to the second temperature, and at the second temperature connected to the connector.

13. An apparatus for testing the PCB assembly as set forth in claim 12, wherein:

the first reservoir receives and stores the first liquid as it drains from the enclosing means, the first reservoir having means for maintaining the first liquid at the first temperature.

14. An apparatus for testing the PCB assembly as set forth in claim 13, further comprising:
   means for draining the second liquid from the enclosing means;
   whereby, the means for testing operation of the PCB assembly further tests operation of the PCB assembly during the change from the second temperature to the first temperature.

15. An apparatus for testing the PCB assembly as set forth in claim 14, wherein:
   the second reservoir receives and stores the second liquid as it drains from the enclosing means, the second reservoir having means for maintaining the second liquid at the second temperature.

16. An apparatus for testing a printed circuit board assembly as set forth in claim 15, further comprising:
   means for draining the second liquid from the enclosure into the second reservoir;
   means for replacing the second liquid with vapor communicated from the second reservoir through the first reservoir to the enclosure; and
   means for communicating the vapor displaced from the enclosure into the first reservoir to condense part of the vapor into the first liquid.

* * * * *

UNITED STATES PATENT AND TRADEMARK OFFICE
CERTIFICATE OF CORRECTION

PATENT NO. : 5,278,495
DATED : January 11, 1994
INVENTOR(S) : Bradford P. Beaton et al.

It is certified that error appears in the above-indentified patent and that said Letters Patent is hereby corrected as shown below:

Column 6, line 8, delete "second" and substitute --first--.

Signed and Sealed this

Twenty-third Day of December, 1997

Attest:

BRUCE LEHMAN

Attesting Officer    Commissioner of Patents and Trademarks